United States Patent
Bales

(10) Patent No.: US 7,128,752 B2
(45) Date of Patent: Oct. 31, 2006

(54) EMBOLI AND THROMBI FILTER DEVICE AND METHOD OF USING THE SAME

(75) Inventor: Thomas O. Bales, Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 533 days.

(21) Appl. No.: 10/328,085

(22) Filed: Dec. 23, 2002

(65) Prior Publication Data

US 2004/0122466 A1   Jun. 24, 2004

(51) Int. Cl.
*A61M 29/00*   (2006.01)

(52) U.S. Cl. ...................................... 606/200

(58) Field of Classification Search ............... 606/200, 606/113, 114, 127, 110
See application file for complete search history.

(56) References Cited

U.S. PATENT DOCUMENTS

| | | | | |
|---|---|---|---|---|
| 4,625,726 A | | 12/1986 | Duthoy | 128/328 |
| 4,706,671 A | * | 11/1987 | Weinrib | 606/159 |
| 4,741,335 A | | 5/1988 | Okada | 128/320 |
| 4,998,539 A | * | 3/1991 | Delsanti | 128/898 |
| 5,357,978 A | * | 10/1994 | Turk | 600/585 |
| 5,449,372 A | * | 9/1995 | Schmaltz et al. | 606/198 |
| 5,456,667 A | * | 10/1995 | Ham et al. | 604/107 |
| 5,910,154 A | * | 6/1999 | Tsugita et al. | 606/200 |
| 6,066,158 A | * | 5/2000 | Engelson et al. | 606/200 |
| 6,264,672 B1 | | 7/2001 | Fisher | 606/200 |
| 6,273,900 B1 | | 8/2001 | Nott et al. | 606/200 |
| 6,325,815 B1 | | 12/2001 | Kusleika et al. | 606/200 |
| 6,336,934 B1 | | 1/2002 | Gilson et al. | 606/200 |
| 6,425,909 B1 | * | 7/2002 | Dieck et al. | 606/200 |
| 6,673,042 B1 | * | 1/2004 | Samson et al. | 604/104 |
| 6,893,451 B1 | * | 5/2005 | Cano et al. | 606/200 |
| 6,902,572 B1 | * | 6/2005 | Beulke et al. | 606/200 |

\* cited by examiner

*Primary Examiner*—Anhtuan T. Nguyen
*Assistant Examiner*—Elizabeth Houston
(74) *Attorney, Agent, or Firm*—Gordon & Jacobson, P.C.

(57) ABSTRACT

A filter basket device includes two shaft wires, a filter basket adapted to capture emboli and thrombi, and an actuation handle. The shaft wires are loosely twisted together so that they remain adjacent to each other, and yet are able to slide relative to each other with little friction and without plastic deformation. One shaft wire is connected to the distal end of the filter basket, and the other shaft wire is connected to the proximal end of the filter basket. The actuation handle moves the shaft wires relative to each other to control opening and closing of the basket. In one embodiment, a guidewire-accepting fitting is attached to a distal portion of the device and permits advancement of the device over a guidewire until a desired location along the guidewire is reached. In another embodiment, the basket is provided with a tip resembling a guidewire.

21 Claims, 1 Drawing Sheet

EMBOLI AND THROMBI FILTER DEVICE AND METHOD OF USING THE SAME

BACKGROUND OF THE INVENTION

1. Field of the Invention

This invention relates broadly to medical devices. More particularly, this invention relates to surgical filter basket devices adapted to retrieve emboli and thrombi in the venous system.

2. State of the Art

Several filter basket devices have been developed for capturing emboli which might be generated during angioplasty or stenting. All such known devices have a shaft which consists of a wire-like central member and a coaxial tubular member which surrounds the central member. A basket (or umbrella) is provided at the distal ends of the central member and stored within the distal end of the tubular member, when not deployed. The basket is deployed by moving the central member distally relative to the tubular member to force the basket out of the tubular member.

In some cases, see e.g., U.S. Pat. No. 6,336,934 to Gilson et al., the basket is anchored to the central wire. In other cases, such as shown in U.S. Pat. No. 6,325,815 to Kusleika et al., the basket floats on the wire, and the wire engages the basket by means of "stops" which come into contact with the basket when the wire is advanced or withdrawn through the sheath, which cause the basket to be pulled from the stored position to the expanded (released) position and vice versa. In all cases, the basket is deployed by moving one or more wires on which the basket is mounted relative to the sheath to force or permit the basket to expand.

The use of the sheath results in such a filter basket device having a minimum diameter no less than the diameter of the sheath, and the sheath must be of sufficient size to receive the wires therethrough. It is important to keep the diameter as small as possible, as the device must be introduced through the small lumen of a guiding catheter to the site of operation. Moreover, the filter basket device may need to be introduced together through the lumen along with other interventional catheter devices, such as angioplasty balloons, stent deployment systems, and stems.

SUMMARY OF THE INVENTION

It is therefore an object of the invention to provide a filter basket device having a relatively small diameter.

It is another object of the invention to provide a filter basket device in which the basket may be deployed and collapsed entirely under control of the physician.

It is a further object of the invention to provide a filter basket device having a collapsible filter adapted to capture and retrieve emboli.

It is also an object of the invention to provide a filter basket device which can be delivered over a guidewire.

In accord with these objects, which will be discussed in detail below, a filter basket device is provided having two shaft wires and a filter basket. The shaft wires are loosely twisted together so that they remain adjacent to each other, and yet are able to slide relative to each other with little friction and without plastic deformation. One of the shaft wires is connected at its distal end to the distal end of the filter basket, and the other of the shaft wires is connected at its distal end to the proximal end of the filter basket. A handle is provided for moving the distal end of one shaft wire relative to the distal end of the other shaft wire.

The filter basket consists of a fabric or a network of wires or filaments, that can be opened (deployed) or closed (collapsed) by moving the ends of the shaft wires relative to each other. If the distal ends of the shaft wires are moved apart, the basket will be collapsed to a small profile, in which state the basket can be easily advanced through a guiding catheter or other sheath into the arterial system. If the distal ends of the shaft wires are moved toward each other, the basket expands. The basket is sized and constructed such that when the basket is expanded inside an artery, the basket will contact the arterial walls and effectively preclude the passage of thrombi and other embolic material downstream.

According to a preferred embodiment of the invention, a guidewire-accepting fitting is attached to a distal portion of the device. In use, once a guidewire has been placed into the desired position in the anatomy, the distal protection device is connected to the guidewire by passing the guidewire-accepting fitting onto the guidewire at a location outside the patient. Once attached, the device can be advanced into the patient by manipulating the handle or by gripping the two shaft wires to track the device along the length of the guidewire until it reaches the desired position near the distal end of the guidewire.

In another embodiment, the distal end of the filter basket can be fitted with a tip resembling a guidewire so that the device can be advanced on its own to the desired location.

The filter basket preferably has a distal portion with fine perforations that allow the passage of blood yet prevent the passage of emboli and thrombi. The proximal portion of the basket is constructed so that there are larger openings to allow the thrombi and emboli to enter the filter basket and be trapped within. Thus, once the filter basket is provided to the necessary location and opened in the artery (and in contact with the arterial wall) thrombi and emboli would be captured inside the filter basket as blood flows through it. The filter basket may then be collapsed and withdrawn, removing the captured thrombi or emboli.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
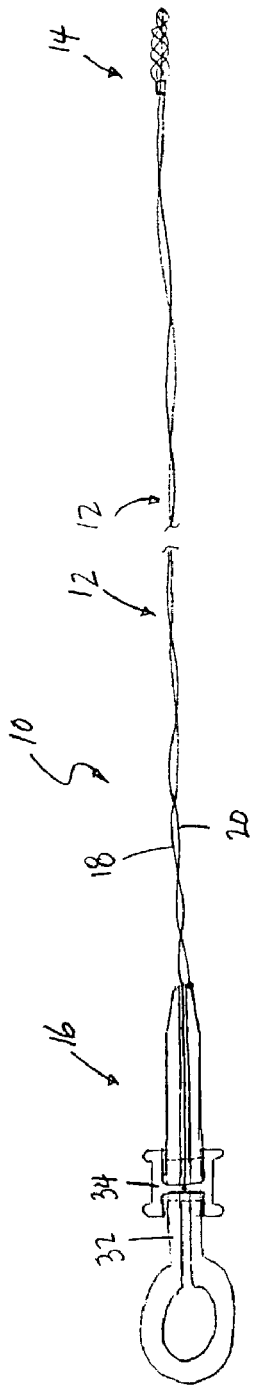
FIG. 1 is a broken side elevation of a filter basket device.
Figure 2:
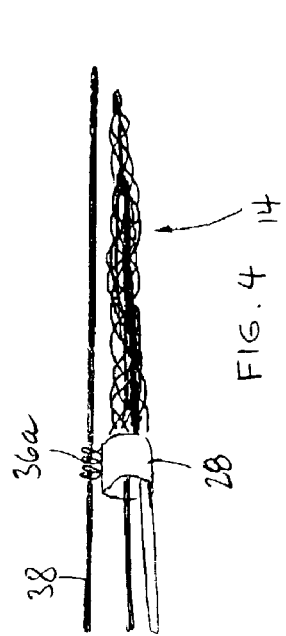
FIG. 2 is a side elevation of a distal end of the filter basket device mounted on a guidewire with a first embodiment of a guidewire mount, with the filter shown in a closed position.

Turning now to FIGS. 1 and 2, the device 10 of die invention includes a shaft portion 12, a filter basket 14 at the distal end of the shaft, and an actuating handle 16. The shaft portion 12 includes two non-concentric shaft wires 18, 20 that are loosely twisted together along their respective lengths so that they remain adjacent to each other, yet are able to slide relative to each other with little friction and without plastic deformation. One of the shaft wires 20 is connected at its distal end 26 to a collar 28 at the proximal end of the filter basket 14 and the other of the shaft wires 18 has a distal end 22 that extends through the collar 23 and is coupled to the distal end 24 of the filter basket 14.

Figure 3:
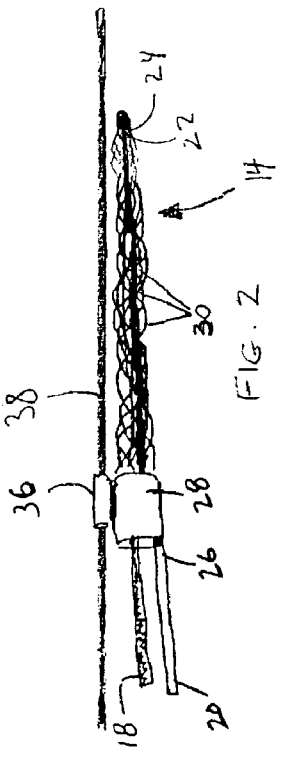
FIG. 3 is a view similar to FIG. 2, with the filter shown in an open position.

Referring to FIGS. 2 and 3, the filter basket 14 consists of a fabric or a network of wires 30 or filaments, discussed below. The basket 14 can be opened (deployed) or closed by moving the distal ends 22, 26 of the shaft wires relative to each other. When the distal ends of the shaft wires are moved apart (as shown in FIG. 2), the basket 14 will be collapsed to a small profile, in which state the basket can be easily advanced through a guiding catheter or other sheath into the arterial system. When the distal ends 22, 26 of the shaft wires are moved toward each other, the basket 14 expands as shown in FIG. 3. The filter basket 14 is sized and constructed such that when the basket is expanded inside an artery, the basket will contact the arterial walls and effectively preclude the passage of thrombi and other embolic material downstream.

Referring back to FIG. 1, the actuating handle 16 includes a stationary first portion 32 and a second portion 34 movable relative to the first portion. By way of example, the actuating handle may be of the shaft and spool type, well known in the endoscopic arts. The proximal end of one of the shaft wires, e.g. wire 18, is coupled to the stationary portion. e.g., by crimping or bonding, and the proximal end of the other of the shaft wires, e.g. wire 20, is coupled to the movable portion. Maintaining the movable second portion 34 relative to the stationary first portion 32, the actuating handle 14 may be manipulated by the physician to position the filter basket 14 into a desired arterial space by pushing and pulling on both wires in tandem. Movement of the second portion 34 relative to the first portion 32 causes the filter basket to open and close. More particularly, when shaft wire 18, which is connected to the distal end 24 of the filter basket 14, is advanced distally (relative to shaft wire 20), the filter basket is moved into the closed configuration (FIG. 2), and when shaft wire 18 is retracted relative to shaft wire 20, the filter basket 14 is moved into an open configuration (FIG. 3).

Referring again to FIGS. 2 and 3, according to a preferred embodiment of the invention, in order to facilitate inserting the filter basket 14 in the arterial system, a guidewire-accepting fitting 36 is attached to a distal portion of the device, such as to the collar 28. In one embodiment, the fitting 36 is a short tube, loop, or hoop. In use, once a guidewire 38 has been placed into the desired position in the anatomy, the basket device 10 is slidably mounted on the guidewire 38 by passing the guidewire-accepting fitting 36 onto the proximal end of the guidewire outside the patient. Alternatively, the distal end of the guidewire may be extended through the fitting prior to insertion of the guidewire into the patient.

Figure 4:
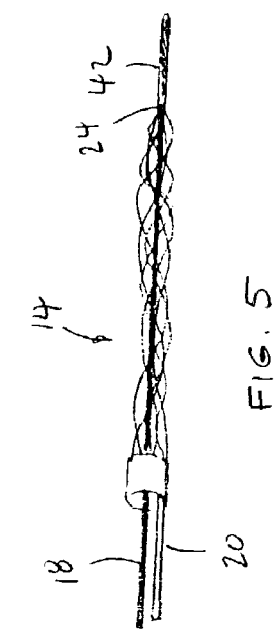
FIG. 4 is a side elevation of a distal end of the filter basket device, shown mounted on a guidewire with a second embodiment of a guidewire mount, and with the filter shown in a closed position.

Referring to FIG. 4, in an alternate embodiment, the fitting is short coil 36a. The coil fitting 36a may be mounted onto a mid-portion of the guidewire 38 (e.g., near where the guidewire enters the body) by wrapping the coil onto the guidewire shaft.

In either embodiment of the fitting, once the basket device 10 is attached to the guidewire 38, the basket filter 14 can be advanced into the patient by manipulating the handle 16 or by directly gripping the two shaft wires 18, 20 to track the device along the length of the guidewire 38 until it reaches the desired position near the distal end of the guidewire.

Figure 5:
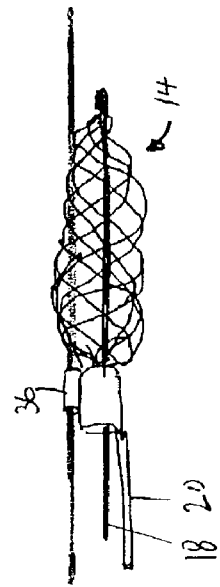
FIG. 5 is a side elevation of a distal end of a second embodiment filter basket device, wherein the filter is provided with a flexible tip.

Referring to FIG. 5, in another embodiment the device 10 is intended to be advanced on its own without tracking along a guidewire. Therefore, no guidewire fitting is provided. Rather, the distal end of the filter basket 14 is fitted with a tip 42 resembling a guidewire. That is, the tip 42 is preferably highly flexible and may be steerable by torquing one or both of the shaft wires 18, 20. In addition, the tip 42 can be an extension the shaft wire 18. Alternatively, the tip can be a separate element joined to the distal end 24 of the filter basket 14.

The filter basket 14 is preferably constructed of a braided network of wires; for example, two intertwined helical sets of wires, with each set extending in a direction opposite to the other set. Alternatively, the filter basket can be constructed of polymer filaments in a braided, woven, or knitted structure, or can be fabricated from one or more pieces of superelastic metal. The basket are constructed having a distal portion with fine perforations that allow the passage of blood yet prevent the passage of emboli and thrombi. The proximal portion of the basket is constructed so that there are larger openings to allow the thrombi and emboli to enter the filter basket and be trapped there. Such a construction is shown and described in detail in U.S. Pat. No. 6,336,934 to Gilson et al., which is hereby incorporated by reference herein in its entirety. In addition, the 'basket' may comprise a filter 'umbrella' attached to a proximal open framework, as shown and described in U.S. Pat. Nos. 6,264,672 to Fisher and 6,273,900 to Nott et al., which are hereby incorporated by reference in their entireties. Thus, once the filter basket is provided to the necessary location and opened in the artery (and in contact with the arterial wall) thrombi and emboli are captured inside the filter basket 14 as blood flows through it. At the end of the procedure, the physician manipulates the handle 16 to move the shaft wires 18, 20 relative to each other to close the filter basket 14, thereby capturing any thrombi or emboli within, and then withdraws the device 10 from the patient.

There have been described and illustrated herein several embodiments of a filter basket device. While particular embodiments of the invention have been described, it is not intended that the invention be limited thereto, as it is intended that the invention be as broad in scope as the art will allow and that the specification be read likewise. Thus, while particular basket constructions have been disclosed, it will be appreciated that other such constructions, particularly those suitable for the capture of thrombi and emboli, can be used as well. In addition, while particular fitting (tubular, loop and coil) have been disclosed, for mounting the basket device over a guidewire, other elements that permit tracking the filter basket device over a guidewire likewise can be used. Moreover, while the device has been explained with respect to its use on a patient, it will be appreciated that it may be used with both human and non-human mammalian subjects, as well as cadavers for experimental and learning uses. It will therefore be appreciated by those skilled in the art that yet other modifications could be made to the provided invention without deviating from its spirit and scope as claimed.

What is claimed is:

1. A surgical filter basket device for use with a guidewire, comprising:
   a) a filter basket having a proximal portion and a distal portion;
   b) a first shaft element having a distal portion coupled to said proximal portion of said filter basket;
   c) a second shaft element having a distal portion coupled to said distal portion of said filter basket, said first and second shaft elements being intertwined relative to each other, yet permitted to move longitudinally relative to each other without plastic deformation; and d) a guidewire mounting means for advancing a portion of said device over the guidewire.

2. A surgical filter basket device according to claim 1, further comprising:
a handle means for moving said first and second shaft elements relative to each other.

3. A surgical filter basket device according to claim 1, further comprising:
a collar coupled to said proximal portion of said filter basket,
wherein said first shaft element is coupled to said collar, and said second shaft element extends through said collar to said distal portion of said filter basket.

4. A surgical filter basket device according to claim 1, wherein:
said guidewire mounting means is one of a tube, a hoop, and a loop.

5. A surgical filter basket device according to claim 1, wherein:
said guidewire mounting means is a coil.

6. A surgical filter basket device according to claim 1, wherein:
said filter basket is comprised of first and second sets of helical wires, said first and second sets being wound in opposite directions relative to each other.

7. A surgical filter basket device according to claim 1, wherein:
said filter basket is comprised of filaments.

8. A surgical filter basket device according to claim 7, wherein:
said filaments are woven.

9. A surgical filter basket device according to claim 1, wherein:
said filter basket defines first openings at said proximal end, and second openings at said distal end, and said first openings are larger than said second openings.

10. A surgical filter basket device, comprising:
a) a filter basket having a proximal portion and a distal portion;
b) a first shaft element having a distal portion coupled to said proximal portion of said filter basket;
c) a second shaft element having a distal portion coupled to said distal portion of said filter basket, said first and second shaft elements being nonconcentric and longitudinally movable relative to each other, wherein such relative longitudinal movement moves said filter basket from between open and closed configurations,
wherein neither of said first and second shaft elements extends within the other; and
d) a guidewire mounting means for advancing a portion of said device over a guidewire.

11. A surgical filter basket device according to claim 10, further comprising:
a handle means for moving said first and second shaft elements relative to each other.

12. A surgical filter basket device according to claim 10, wherein:
said guidewire mounting means is one of a tube, a hoop, and a loop.

13. A surgical filter basket device according to claim 10, wherein:
said guidewire mounting means is a coil.

14. A surgical filter basket device according to claim 10, wherein:
said filter basket is comprised of first and second sets of helical wires, said first and second sets being wound in opposite directions relative to each other.

15. A surgical filter basket device according to claim 10, wherein:
said filter basket is comprised of filaments.

16. A surgical filter basket device according to claim 15, wherein:
said filaments are woven.

17. A surgical filter basket device according to claim 10, wherein:
said filter basket defines first openings at said proximal portion and second openings at said distal portion, wherein said first openings are larger than said second openings.

18. A surgical filter basket device for use with a guidewire, comprising:
a) a filter basket having proximal and distal portions;
b) a shaft including a first element having a distal portion coupled to said proximal portion of said filter basket, and a second element having a distal portion coupled to said distal portion of said filter basket, said first and second elements being intertwined relative to each other along their respective lengths, yet permitted to move longitudinally relative to each other without plastic deformation, wherein such relative longitudinal movement moves said filter basket from between open and closed configurations; and
c) a fitting coupled to one of said filter basket and said shaft element, said fitting adapted to be slidably mounted over the guidewire.

19. A surgical filter basket device according to claim 18, wherein:
said fitting includes one of a tube, a hoop, and a loop.

20. A surgical filter basket device according to claim 18, wherein:
said fitting includes a coil.

21. A surgical filter basket device according to claim 18, further comprising:
d) a handle means for moving said first and second elements relative to each other.

* * * * *